United States Patent [19]
Allard et al.

[11] Patent Number: 6,107,049
[45] Date of Patent: Aug. 22, 2000

[54] SANDWICH IMMUNOASSAY DETERMINATION OF CPSA

[75] Inventors: William Jeffrey Allard, Poughquag, N.Y.; Kwok K. Yeung, Ridgefield, Conn.; Zeqi Zhou, New City, N.Y.

[73] Assignee: Bayer Corporation, Tarrytown, N.Y.

[21] Appl. No.: 08/986,480

[22] Filed: Dec. 8, 1997

Related U.S. Application Data

[60] Division of application No. 08/903,750, Jul. 31, 1997, Pat. No. 5,840,501, which is a continuation-in-part of application No. 08/834,969, Apr. 7, 1997, abandoned, which is a continuation-in-part of application No. 08/738,383, Oct. 25, 1996, abandoned.

[51] Int. Cl.$^7$ .................. G01N 33/53; G01N 33/577; G01N 33/543; C07K 16/18
[52] U.S. Cl. .................. 435/7.1; 435/7.4; 435/7.5; 435/7.6; 435/7.9; 435/7.92; 435/7.93; 435/7.94; 435/975; 436/524; 436/518; 530/388.26; 530/388.25; 530/389.1; 530/389.3; 530/389.7; 530/388.8
[58] Field of Search .................. 435/7.4, 7.1, 7.5, 435/7.6, 7.9, 7.92, 7.93, 7.94, 975; 530/388.26, 388.25, 389.3, 389.1, 389.7, 388.8; 436/524, 518

[56] References Cited

U.S. PATENT DOCUMENTS

| 5,501,983 | 3/1996 | Lilja et al. . |
| 5,599,677 | 2/1997 | Dowell et al. . |

FOREIGN PATENT DOCUMENTS

| 0635575 | 6/1994 | European Pat. Off. . |
| 4322342 | 7/1993 | Germany . |
| 62-46263 | 2/1987 | Japan . |
| 9626441 | 8/1996 | WIPO . |
| WO 96/26441 | 8/1996 | WIPO . |
| 9712245 | 4/1997 | WIPO . |

OTHER PUBLICATIONS

Stenman UH, Leinonen J, Alfthan H, Rannikko S, Tuhkanen K, Alfthan O. A complex between prostate–specific antigen and alpha–121–antichymotrypsin is the major form of prostate–specifi antigen in serum of patients with prostatic cancer: assay of the complex improves clinical sensitivity for cancer. Cancer Res 1991; 51:222–226.

Zhou AM, Tewari PC, Bluestein BL, Caldwell GW, Larsen FL. Multiple forms of prostate–specific antigen in serum: differences in immunorecognition by monoclonal and polyclonal assays. Clin Chem 1993; 39:2483–91.

Leinonen J, Lovgren T, Vornanen T, Stenman UH. Double–label time–resolved immunoflurometric of prostate–specific antigen and its complex with alpha$_1$–antichymotrypsin Clin Chem 1993; 39:2098–2103.

Christensson A, Bjork T, Nilsson O, Dahlen U, Matikainen MT, Cockett AT, Abrahamsson PA. Serum prostate specific antigen complexed with alpha$_1$=antichymotrypsin as an indicator of prostate cancer. J Urol 1993; 159:100–105.

Lilja H. Significance of different molecular forms of serum PSA. The free, noncomplexed forms of PSA versus that complexed to alpha$_1$–antichymotrypsin. Urol Clin North Am 1993; 20(4):681–686.

Lilja H, Christensson A, Dahlen U, Matikainen MT, Nilsson O, Pettersson K & Lovgren T. Prostate–specific antigen in human serum occurs predominantly in complex with alpha–antichymo–trypsin. Clin Chem 1991; 37:1618–1625.

Bjork T, Hulkko S, Bjartell A, Santagnese AD, Abrahamsson PA, Lilja H. Alpha$_1$–antichymotrypsin production in PSA–producing cells is common in prostate cancer but rate in benign prostatic hyperplasia. Urology 1994; 43:427–434.

Pettersson K, Piironen T, Seppala M, Liukkonen L, Christensson A, Matikainen MT, Suonpaa M, Lovgren T, Lilja H. Free and complexed prostate–specific antigen (PSA): in vitro stability, epitope map, and devleopment of immunoflurometric assays for specific and sensitive detection of free PSA and PSA–alpha$_1$–antichymotrypsin complex. Clin chem 1995; 41:1480–1488.

Wu JT, Wilson L, Zhang P, Meikle AW, Stephenson R. Correlation of serum concentraitons of PSA–ACT complex with total PSA in random and serial specimens from patients with PBH and prostate cancer. J. Clin Lab Anal 1995; 9:15–24.

Mitrunen K, Pettersson K, Piironen T, Bjork T, Lilja H, Lovgren T. (1995) Duel label one–step immunoassay for simultaneous measurement of free and total prostate specific antigen concentraiton and ratios in serum. Clin Chem 1995 41(8):1115–1120.

Catalona WJ, Smith DS, Wolfert RL, Wang TJ, Rittenhouse HG, Ratliff TL, Nadler RB. Evaluation of percentage of free serum prostate–specific antigen to improve specificity of prostate cancer screening. JAMA 1995; 274(15): 1214–1220.

Prestigiacomo AF, Stamey TA. Clinical usefulness of free and complexed PSA. Scan J. Clin Lab Invest 1995; 55Suppl221:32–34.

(List continued on next page.)

*Primary Examiner*—David Saunders
*Assistant Examiner*—F. Pierre VanderVegt
*Attorney, Agent, or Firm*—Andrew L. Klawitter

[57] ABSTRACT

A method for determining the complexed forms of immunologically determinable prostate specific antigen (cPSA) in a blood sample, e.g., by two-site immunometric assays, in which the blood sample is treated to render free PSA (fPSA) immunologically nondetectable. A particularly preferred immunometric assay method employs three anti-PSA antibodies: an antibody that binds to both cPSA and fPSA (anti-tPSA), a second anti-tPSA antibody which is characterized by the unique property that binding to fPSA is blocked by binding of fPSA-specific antibodies, and a third antibody which is a fPSA-specific antibody. Thus, binding of the fPSA-specific antibody to PSA in the sample allows only cPSA to be measured in the immunometric assay. Measurement of cPSA blood levels has been found to provide a method for aiding in the diagnosis and monitoring of prostate cancer that is highly sensitive and specific, and eliminates the need for a significant number of patients to undergo unnecessary prostate biopsy.

20 Claims, 11 Drawing Sheets

OTHER PUBLICATIONS

Wang TJ, Hill TM, Sokoloff RL, Frankenne F, Rittenhouse HG, Wolfert RL, Duel monoclonal antibody immunoassay for free prostate–specific antigen. Prostate 1996; 28:10–16.

Jung K, Stephan C. Lein M, Henkne W, Schnorr D, Brux B, Schurenkamper P, Loening SA. Analytical performance and clinical validity of two free prostate–specific antigen assays compared. Clin Chem 1996; 42(7):1026–1033.

Wang TJ, Hill T, Sokoloff R, Frankenne F, Wolfert R and Rittenhouse H. Monoclonal antibody sandwich immunoassay to quantitate free PSA in benign hyperplasia and prostate cancer. Poster presentation at 1994 ISOBM meeting.

Chan D, Kelley CA, Partin AW, Linton J, Want TJ, Sokoloff RL, Rittenhouse HG, and Wolfert RL. Clin Chem (1996) 42(6):S255.

Wang TJ, Linton HJ, Payne J, Liu RS, Kuus–Reichel K, Rittenhouse HG, Kelley C, Cox J, Chan DW, and Wolfert RL. Development of monoclonal antibodies specific for the PSA–ACT complex and their incorporation into an immunoassay. Clin Chem (1997); 43(6):S255.

Zhang P and Wu JT. Development of an immunoassay for the PSA–ACT complex in serum without interference of non–specific adsorption. Clin Chem (1997) 43(6):S236.

Bjork T, Bjartell A, Abrahamsson PA, Hulkko S, Di Sant'agnese A, Lilja H. Alpha$_1$–antichymotrypsin production in PSA–producing cells is common in prostate cancer but rare in benign prostatic hyperplasia. Urol 1994; 43(4):427–434.

Carter HB, Pearson JD, Metter J, Brant LJ, Chan DW, Andres R, Fozard JL and Walsh PC. Longitudinal evaluation of prostate–specific antigen levels in men with and without prostate disease. JAMA 1992; 267(16):2215.

J. Leinonen et al: "Complex Formation betweenPSA isoenzymes and protease inhibitors." The Journal of Urology, vol. 155, No. 3, Mar. 1996, pp. 1099–1103.

Kramer BS et al: "Prostate Cancer Screening: What We Know and What We Need to Know." Annals of Internal Medicine, vol. 119, No. 9, Nov. 1, 1993, pp. 914–923.

| SAMPLE | FORMAT 1 REACTION RATE (mA/min) -PSA20 | FORMAT 1 REACTION RATE (mA/min) +PSA20 | FORMAT 1 % INHIBITION | ASSAY FORMAT 2 REACTION RATE (mA/min) -PSA20 | ASSAY FORMAT 2 REACTION RATE (mA/min) +PSA20 | ASSAY FORMAT 2 % INHIBITION |
|---|---|---|---|---|---|---|
| 1 | 40.6 | 2.2 | 95 | 36.5 | 1.1 | 97 |
| 2 | 229.7 | 11 | 95 | 168 | 10.7 | 94 |
| 3 | 447 | 27 | 94 | 395 | 24.6 | 94 |

FIG. 3

| POPULATION* | SENSITIVITY | | | | SPECIFICITY | | | |
|---|---|---|---|---|---|---|---|---|
| | n | tPSA % | t+f/t## % | cPSA# % | n | tPSA % | t+f/t % | cPSA % |
| ALL | 53 | 88 | 83 | 85 | 163 | 75 | 82 | 80 |
| 0-20+ | 74 | 85 | 85 | 81 | 190 | 70 | 79 | 76 |
| 0-10+ | 46 | 76 | 74 | 70 | 178 | 76 | 82 | 81 |
| 4-10+ | 35 | 100 | 97 | 91 | 43 | 0 | 26 | 23 |

\* BASED ON TOTAL PSA VALUES

\*\* SENSITIVITY AND SPECIFICITY BASED ON AN UPPER LIMIT OF NORMAL OF 4.0 ng/ml

\# SENSITIVITY AND SPECIFICITY BASED ON AN UPPER LIMIT OF NORMAL OF 3.75 ng/ml

\#\# SENSITIVITY AND SPECIFICITY FOR tPSA BASED ON ULN=4.0; AND AN ULN FOR f/t RATIO OF 25%

+ INCLUDES PATIENTS SELECTED FOR VALUES IN THE 0-20 ng/ml RANGE

FIG.4A

| POPULATION* | SENSITIVITY | | | | SPECIFICITY | | | |
|---|---|---|---|---|---|---|---|---|
| | n | tPSA** % | t+f/t ## % | cPSA # % | n | tPSA % | t+f/t % | cPSA % |
| ALL | 75 | 83 | 77 | 81 | 225 | 33 | 44 | 48 |
| 0 - 20 | 72 | 82 | 76 | 81 | 223 | 34 | 44 | 49 |
| 0 - 10 | 49 | 73 | 69 | 71 | 192 | 39 | 49 | 57 |
| 4 - 10 | 36 | 100 | 94 | 97 | 117 | 0 | 17 | 29 |

\* BASED ON TOTAL PSA VALUES

\*\* SENSITIVITY AND SPECIFICITY BASED ON AN UPPER LIMIT OF NORMAL OF 4.0 ng/ml

\# SENSITIVITY AND SPECIFICITY BASED ON AN UPPER LIMIT OF NORMAL OF 3.75 ng/ml

\#\# SENSITIVITY AND SPECIFICITY FOR tPSA BASED ON ULN=4.0; AND AN ULN FOR f/t RATIO OF 25%

FIG.4B

| POPULATION* | SENSITIVITY# | | | | SPECIFICITY | | | |
|---|---|---|---|---|---|---|---|---|
| | cPSA | | PSA-ACT | | cPSA | | PSA-ACT | |
| | n | % | n | % | n | % | n | % |
| All | 53 | 85 | 86 | 88 | 163 | 80 | 165 | 72 |
| 0 - 20* | 74 | 81 | 79 | 88 | 190 | 76 | 159 | 74 |
| 0 - 10* | 46 | 70 | 53 | 82 | 178 | 81 | 150 | 79 |
| 4 - 10* | 35 | 91 | 40 | 100 | 43 | 23 | 40 | 20 |

*Based on total PSA values
Sensitivity andSpecificity based on an upper limit of normal of 3.75 ng/ml
*Includes patients selected for values in the 0 - 20 ng/ml range

Fig. 6

SPECIFICITY OF PSA ASSAYS AT SELECTED SENSITIVITIES

| % SENSITIVITY | tPSA CUT-OFF | tPSA %SPECIFICITY | cPSA CUT-OFF | cPSA %SPECIFICITY | f/tPSA RATIO CUT-OFF | f/tPSA RATIO %SPECIFICITY |
|---|---|---|---|---|---|---|
| ALL SAMPLES ||||||||
| 80 | 4.11 | 35.6 | 3.98 | 51.6 | 19 | 46.2 |
| 85 | 3.86 | 31.1 | 3.34 | 38.7 | 22 | 32.4 |
| 90 | 3.4 | 25.3 | 2.94 | 33.8 | 24 | 26.2 |
| 95 | 3.06 | 21.8 | 2.52 | 26.7 | 28 | 15.6 |
| 97.5 | 2.28 | 12.9 | 1.67 | 14.7 | 32 | 8.9 |
| 100 | 1 | 3.1 | 0.89 | 6.2 | 67 | 0 |
| 4-10 ng/ml tPSA ONLY ||||||||
| 80 | 5.27 | 38.1 | 4.55 | 43.9 | 20 | 29.8 |
| 85 | 4.66 | 22.9 | 4.21 | 34.2 | 22 | 25.4 |
| 90 | 4.01 | 0.8 | 3.92 | 25.4 | 24 | 19.3 |
| 95 | 3.99 | 0 | 3.36 | 7.9 | 29 | 11.4 |
| 100 | 4 | 0 | 3.26 | 7 | 34 | 4.4 |

FIG.7

SANDWICH IMMUNOASSAY DETERMINATION OF CPSA

CROSS-REFERENCE TO RELATED APPLICATION

This is a division of application Ser. No. 08/903,750, filed Jul. 31, 1997, now U.S. Pat. No. 5,840,501, which is a continuation-in-part of application Ser. No. 08/834,969, filed Apr. 7, 1997, now abandoned, which is a continuation-in-part of application Ser. No. 08/738,383, filed Oct. 25, 1996, now abandoned.

BACKGROUND OF THE INVENTION

The present invention relates to the determination of the complexed forms of immunologically determinable prostate specific antigen (PSA) in a blood sample. More particularly, the invention relates to the determination of complexed PSA by two-site immunometric assay and the clinical significance of complexed PSA assay values.

Human prostate specific antigen (PSA) is a glycoprotein of approximately 33,000 daltons with high amino acid homology to the human kallikrein family (1,2) and has been shown to be a serine protease with trypsin and chymotrypsin-like activity (3,4,5). PSA is secreted by epithelial cells of the prostate gland and is one of the major proteins found in seminal fluid (6). Following the discovery that the concentration of PSA increases in the serum of patients with prostate cancer, numerous reports have established this protein as an important and clinically useful biomarker for the management of prostate cancer patients (7,8,9,10). Recent efforts have focused on the use of serum PSA testing for early detection of prostate cancer in asymptomatic men. In fact, the American Cancer Society and the American Urological Society have recently recommended that all men over the age of 50 be screened annually using serum PSA in conjunction with digital rectal examination (DRE) (11).

The clinical value of early detection of prostate cancer remains controversial for several reasons. First, it is unclear whether treatment of prostate cancer at early stages will improve survival in the affected population. Clinical trials designed to address this issue are currently underway. Second, a clinical trial recently measured the effectiveness of serum PSA measurements in conjunction with digital rectal examination (DRE) for early detection of prostate cancer in men over 50 years of age (12). Of the 1060 patients who had either an abnormal DRE or an elevated PSA test, only 22% had prostate cancer. These data demonstrate that 70–80% of all prostate biopsies are performed on men who do not have cancer. Since 30–50% of men over the age of 50 have evidence of prostate cancer on autopsy, the number of unnecessary prostate biopsies triggered by elevated PSA assays could be very high. This has consequences both in increased medical costs and increased morbidity associated with the biopsy procedure.

Several laboratories have shown independently that PSA forms complexes with protease inhibitors such as $\alpha_1$-antichymotrypsin (ACT), $\alpha_2$-macroglobulin, and $\alpha_1$-antitrypsin (13–19). PSA in complex with ACT or $\alpha_1$-antitrypsin or in free, uncomplexed form is detectable in serum by immunoassay techniques. Indeed, the majority of immunoreactive PSA in serum is complexed with ACT, and a significant correlation has been established between the proportion of PSA bound to ACT and total serum PSA concentration (13). PSA bound to $\alpha_2$-macroglobulin, however, is not measurable in serum due to steric hindrance of antibody binding to PSA following complexation with this protease. In early work, PSA-ACT levels and the proportion of PSA-ACT to total PSA were suggested to be of use in prostate cancer diagnosis (13,15,16,17), however, for a variety of reasons (some of which are discussed below) it has been difficult to draw conclusions on the clinical utility of serum measurement of PSA-ACT.

Lilja, Stenman, and coworkers published in 1991 that serum PSA exists in free form and in complexes with ACT and $\alpha_1$-antitrypsin (13,18). In subsequent work, Stenman et al. demonstrated that measurement of PSA-ACT in association with measurement of free plus complexed PSA (termed total PSA, although PSA complexed with $\alpha_2$-macroglobulin is not measured by conventional PSA assays) may improve discrimination between men with prostate cancer and those with benign prostate disease such as benign prostatic hypertrophy (BPH). However, the accurate measurement of PSA-ACT complexes has not been attainable due to technical problems in accurate measurement of the complex. Stenman et al. found that the correlation of PSA-ACT values with total PSA measurement was not good at the low end and the y intercept was elevated indicating over-recovery of complexed PSA (13 and U.S. Pat. No. 5,501,983). Indeed, they found that for most patients tested, the concentration of PSA-ACT was higher than for total PSA (U.S. Pat. No. 5,501,983). Subsequent correlation analysis for complexed and free PSA showed a slope of 1.12 indicating over-recovery of the PSA-ACT complex (16). Pettersson et al. addressed this over-recovery when they found elevated PSA-ACT values in female sera (20). While the addition of heparin reduced the incidence of false positive values in female serum, more recent attempts to measure PSA-ACT complexes in patients with prostate cancer and BPH continue to show significant over-recovery of complexes (21).

Because of the difficulties encountered in the measurement of PSA-ACT complexes, attention in the literature turned to the measurement of free, uncomplexed PSA in conjunction with measurement of total PSA. It is now clear that improved specificity is needed when total PSA values range from about 4–10 ng/mL. When serum total PSA is <4.0 ng/mL, the risk of prostate cancer is low; similarly, when total PSA is >10 ng/mL, the risk of prostate cancer is >50% and prostate biopsy is indicated. Within the diagnostic gray zone (generally between 2–20 ng/mL, more commonly between 4–10 ng/mL) the risk of cancer is high, but the rate of false positives is also high. The retrospective application of a ratio of free PSA/total PSA has shown that the specificity of total PSA in the 4–10 ng/mL gray zone could be improved from approximately 50–60% to 70–80% (22–26). This improved specificity could result in a 20–30% decrease in unnecessary biopsies. PCT WO 96-26441 and WO 97-12245 similarly describe the use of the free PSA/total PSA ratio to improve discrimination between BPH and cancer, respectively, in patients with total PSA levels between 2.5 and 20 ng/mL.

The measurement of free PSA has technical difficulties of its own, however. First, within the diagnostic gray zone, the proportion of free PSA is typically quite low, in the 5–30% range. A successful free PSA assay must, therefore, measure accurately in the range of 0.2–3.0 ng/mL. Also, the concentration of free PSA is not significantly different in patients with BPH and cancer, and the ratio of free PSA/total PSA decreases due to an increase in the proportion of PSA complexed to ACT. In addition, free PSA is not stable in serum and levels of free PSA have been known to decrease over time, presumably due to complexation with $\alpha_2$-macroglobulin.

In the meantime, there has been further acknowledgment of the problems associated with the accurate measurement of PSA-ACT in blood, coupled with attempts to overcome such problems. In 1994, workers at Hybritech reported the development of a sandwich immunoassay for PSA-ACT employing anti-PSA and anti-ACT antibodies. They concluded that the measured PSA-ACT values failed to demonstrate improved clinical specificity in the diagnosis of prostate cancer (27). Later, this group jointly with workers at the Johns Hopkins Medical Institutions reported the finding that the anti-PSA/anti-ACT sandwich immunoassay method suffers from significant non-specific binding and over recovery of PSA-ACT. Unless resolved, they concluded that these problems rendered the measurement of PSA-ACT clinically meaningless (28). Subsequently, this joint group reported having overcome the non-specific binding problem through the development of a sandwich immunoassay for PSA-ACT based on a monoclonal antibody specific for PSA-ACT complex (29, 30). However, their clinical studies failed to show any improvement in specificity for prostate cancer by measuring PSA-ACT complex alone compared with measurement of total PSA or with a calculated ratio of PSA-ACT to total PSA (29). Other approaches to overcoming the problems associated with PSA-ACT measurement have been proposed, including the use of blocking agents (31).

It remains unclear why the proportion of PSA complexed to ACT increases in patients with prostate cancer, but it may be related to the observation that antibodies to ACT do not stain prostatic epithelium from BPH patients and mRNA transcripts are not found in such tissue. In contrast, anti-ACT immunoreactivity and mRNA synthesis are detected in prostatic epithelium from patients with prostate cancer (32). These results suggest that in prostate tumors, PSA may complex in situ with ACT prior to release into serum. An alternative mechanism may involve the access of active PSA to the blood stream. Free PSA found in serum from healthy men is proteolytically cleaved and enzymatically inactive. Tumors, however, synthesize angiogenic factors which lead to increased vascularization of tumor tissues. It may be that in tumors, a larger proportion of enzymatically active PSA gains access to the blood stream. This active PSA would be expected to complex with protease inhibitors such as ACT leading to a higher proportion of PSA-ACT complex in serum from prostate cancer patients.

Accordingly, there is a need for an accurate method of determining complexed PSA and to assess the clinical significance of blood levels of complexed PSA relative to screening of male patients for prostate cancer.

EP 635,575 describes the preparation of monoclonal antibodies that bind to free PSA but not PSA-ACT.

PCT WO 95/18381 relates to a monoclonal/polyclonal immunometric assay method for the determination of PSA which is rendered capable of providing an equimolar response to free and complexed PSA by the addition of antibody that binds to free PSA but not complexed PSA.

U.S. patent application Ser. No. 08/595,155 now abandoned, and Zhou Z., Ng PC, Very DL, Allard W. J., Yeung K. K., J. Clin. Lab. Anal. (1996), 10:155–159, describe a method for preparing a monoclonal antibody that provides an equimolar response to free and complexed PSA in a monoclonal/polyclonal immunometric assay. The described monoclonal antibody has the unique property of binding to PSA to render PSA substantially incapable of binding with antibodies that bind free PSA but not complexed PSA.

Published Japanese Patent Document 62-46263 describes a sandwich immunoassay method for the determination of PSA in complex with protease inhibitor.

Published German Patent Application 4,322,342 describes a method for measuring both total PSA and PSA-ACT in a single assay for the purpose of providing values for calculation of the ratio of PSA-ACT to total PSA.

Chichibu et al, in the Journal of Medicine and Pharmaceutical Science (Japan, 1996) 36(3): 477–483, describe a sandwich immunoassay for PSA-ACT employing anti-PSA bound to a bead and enzyme-labeled anti-ACT. Data establishing the ability to accurately measure PSA-ACT in a blood sample is lacking.

SUMMARY OF THE INVENTION

The present invention provides a method for determining complexed PSA (herein referred to as cPSA) in a blood sample by treating the blood sample to render uncomplexed, i.e., free, PSA (fPSA) nondetectable by immunoassay, and then determining PSA in the treated blood sample by immunoassay whereby only cPSA is detectable. The immunoassay can be performed in any conventional manner, but more usually is a competitive immunoassay or a two-site immunometric assay. The present method can be accomplished in a variety of ways as described in more detail below. In general, such methods include separation methods in which fPSA is physically removed or retained from the immunoassay test mixture, as well as methods in which an antigenic determinant or determinants in fPSA are modified, such as by chemical interaction, to render fPSA essentially unable to bind to antibody used in the immunoassay method, thereby effectively eliminating fPSA from the assay.

A particularly advantageous two-site immunometric assay method has been devised based on a three antibody reagent system:

(a) a first anti-PSA antibody (monoclonal or polyclonal) which binds to tPSA and which participates in the immunometric assay, (b) a second anti-PSA antibody (preferably monoclonal) which also binds to tPSA and which also participates in the immunometric assay, but which is selected to have the property that it is substantially incapable of binding to PSA when PSA is bound by a fPSA-specific antibody (this second antibody is referred to herein at times as "MM1"), and (c) a third anti-PSA antibody which is fPSA-specific, and preferably is monoclonal.

As participants in the immunometric assay, one of the first and second anti-PSA antibodies is labeled for detection purposes (and can be referred to as the "labeled" or "detection" antibody) and the other is immobilized or is capable of being immobilized for purposes of separation from the test mixture (the "capture" antibody). Accordingly, assay conditions can be established under which fPSA in a blood sample will bind with the fPSA-specific (third) antibody, rendering fPSA from the sample incapable of binding with the aforesaid MM1 (second) antibody. Since the two-site immunometric assay is dependent upon the binding of both of the aforesaid first and second antibodies (the "labeled" and "capture" antibodies) to PSA, binding of the fPSA-specific antibody consequently renders the fPSA form incapable of detection by the two-site immunometric assay. It will be noted that despite the fact that the three antibodies used in this particularly unique assay system are all specific for one or more forms of PSA (that is, none are directed to any of the protease inhibitors comprised in cPSA), the particular properties of the antibodies permit the specific determination of cPSA.

It has been found that the measurement of cPSA blood levels provides a highly sensitive and specific method for detecting prostate cancer (CaP). cPSA assays also have the advantage of increased analytical accuracy compared to assays involving the measurement of fPSA since cPSA is the predominant form of PSA and environmental and analytical factors (e.g., sample age) affecting the distribution of PSA between the fPSA and cPSA forms produce a much lower effect on the accuracy of cPSA measurements by comparison with measurements of fPSA.

Since cPSA is comprised primarily of PSA complexed with the protease inhibitor $\alpha_1$-antichymotrypsin (ACT), PSA-ACT-specific assays will also yield the advantageous sensitivity, specificity, and other features of the cPSA assays.

BRIEF DESCRIPTION OF THE DRAWINGS

FIG. 3 is a table showing that PSA 20 can be used to automate the cPSA assay on an automated immunoanalyzer. Assay format 1 used MAb PSA 20 added to the MM1-fluorescein conjugate (R1) with a total incubation time of 38 minutes. Assay format 2 used an on-board preincubation of PSA MAb 20 with the samples and a total incubation time of 78 minutes. All results are presented as the rate of color formation.

FIGS. 4A and 4B are tables summarizing results of measurement of total, free, and complexed PSA in the serum of men with prostate cancer, BPH or in healthy age-matched controls. The unselected patient population designated "All" includes patient samples derived from men with CaP, BPH, or healthy age-matched controls without regard to tPSA values. When patient groups were stratified according to tPSA value, additional patient samples were included in the analysis shown in FIG. 4A and in the cPSA portion of the analysis shown in FIG. 4B, which additional samples were selected by tPSA values for inclusion in the diagnostic gray zone as described in the specification below.

FIG. 6 is a table summarizing results of measurement of cPSA and PSA-ACT in the serum of men with prostate cancer, BPH or in healthy age-matched controls. The unselected population (designated "All") and the patient groups stratified according to tPSA level were identical to those used in the studies summarized in FIGS. 4A and 4B.

FIG. 7 is a table showing correlations of cut-off values (i.e., upper limits of normal) and specificity at selected sensitivities among assay values obtained by a commercial tPSA assay, by a preferred cPSA assay, and by calculation of fPSA/tPSA ratios.

DESCRIPTION OF THE PREFERRED EMBODIMENTS

Figure 1A:
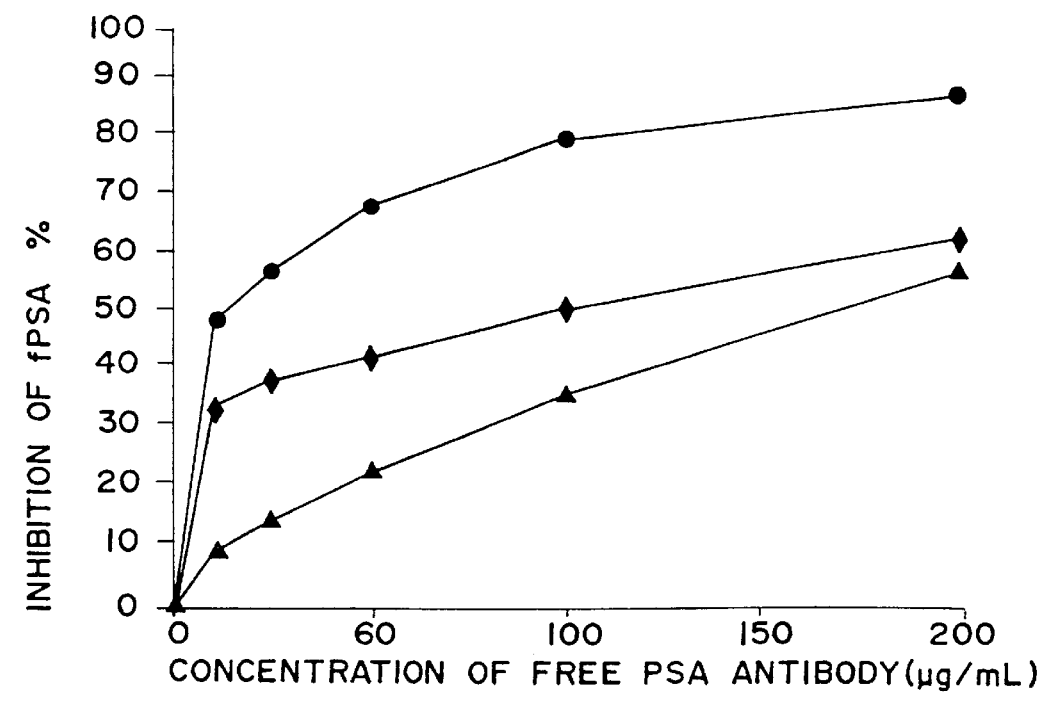
FIG. 1A is a graph showing the inhibition of fPSA immunoreactivity in a two-site immunometric assay for tPSA in the presence of three different monoclonal antibodies to the E-epitope of PSA. Samples containing fPSA at 50 ng/mL were preincubated with each anti-fPSA MAb for 30–60 minutes and run in the Bayer Immuno 1™ tPSA Assay.

As used herein, the following terms shall have the indicated meanings:

PSA shall mean prostate specific antigen.

tPSA or total PSA shall mean the total amount of immunologically determinable PSA in a blood sample, that is, PSA in complexed or free forms that are capable of responding to measurement by conventional immunoassays. Based on current knowledge, it is understood that blood PSA that is complexed with certain protease inhibitors (including ACT, $\alpha_1$-antitrypsin, and inter-$\alpha$ trypsin inhibitor) is immunologically determinable, whereas PSA is not determinable when complexed with such other protease inhibitors as $\alpha_2$-macroglobulin.

fPSA or free PSA shall mean PSA in its free, uncomplexed form. cPSA or complexed PSA shall mean tPSA that is not fPSA.

E-epitope shall mean the collection of epitopes on PSA which are binding sites for antibodies which bind to fPSA but not to cPSA.

Anti-E antibodies shall mean antibodies which bind to E-epitope, and thus are specific for binding fPSA.

Antibody shall mean whole immunoglobulin, e.g., IgG or IgM, or an immunoglobulin fragment comprising an antibody binding site, e.g., Fab, Fab', and F(ab')$_2$ fragments, or aggregates thereof.

The present invention provides means for determining cPSA in a blood sample by measuring tPSA by immunoassay after rendering fPSA in the blood sample nondetectable. It will be evident to one of ordinary skill in the art that a variety of immunoassay methods can be used to measure tPSA and that a variety of means can be employed to render fPSA in the blood sample nondetectable.

In general, tPSA immunoassay methods are either competitive or noncompetitive. The former methods typically employ an immobilized or immobilizable antibody to PSA (anti-PSA) and a labeled form of PSA. Sample PSA and labeled PSA compete for binding to anti-PSA. After separation of the resulting labeled PSA that has become bound to anti-PSA (bound fraction) from that which has remained unbound (unbound fraction), the amount of the label in either bound or unbound fraction is measured and can be related to the amount of PSA in the test sample in any conventional manner, e.g., by comparison to a standard curve.

Non-competitive methods are more commonly used for the determination of tPSA, with the most common method being the two-site immunometric assay method (sometimes referred to as the "sandwich" method). In immunometric assays, two anti-PSA antibodies are employed. One of the anti-PSA antibodies is labeled (sometimes referred to as the "detection antibody") and the other is immobilized or immobilizable (sometimes referred to as the "capture antibody"). As is known in the art, the capture and detection antibodies can be contacted simultaneously or sequentially with the test sample. Sequential methods can be accomplished by incubating the capture antibody with the sample, and adding the labeled antibody a predetermined time thereafter (sometimes referred to as the "forward" method); or the detection antibody can be incubated with the sample first and then the labeled antibody added (sometimes referred to as the "reverse" method). After the necessary incubation(s) have occurred, to complete the assay, the capture antibody is separated from the liquid test mixture, and the label is measured in at least a portion of at least one of the separated capture antibody phase or the remainder of the liquid test mixture, normally the former since it comprises PSA bound by ("sandwiched" between) the capture and detection antibodies.

In typical two-site immunometric assays for PSA, one or both of the capture and detection antibodies are monoclonal antibodies. The label used in the detection antibody can be selected from any of those known conventionally in the art. Commonly, the label is an enzyme or a chemiluminescent moiety, but can also be a radioactive isotope, a fluorophor, a detectable ligand (e.g., detectable by a secondary binding by a labeled binding partner for the ligand), and the like. The important property of the capture antibody is that it provides a means for being separated from the remainder of the test mixture. Accordingly, as is understood in the art, the capture antibody can be introduced to the assay in an already immobilized or insoluble form, or can be in a immobilizable form, that is, a form which enables immobilization to be accomplished subsequent to introduction of the capture antibody to the assay. Examples of immobilized capture antibody are antibody covalently or noncovalently attached to a solid phase such as a magnetic particle, a latex particle, a microtiter plate well, a bead, a cuvette, or other reaction vessel. An example of an immobilizable capture antibody is antibody which has been chemically modified with a ligand moiety, e.g., a hapten, biotin, or the like, and which can thus be subsequently immobilized by contact with an immobilized (as described above for directly immobilized capture antibody) form of a binding partner for the ligand, e.g., an antibody, avidin, or the like.

The above-described immunoassay methods and formats are intended to be exemplary and are not limiting since, in general, it will be understood that any immunoassay method or format can be used in the present invention.

It will also be understood that the means employed for rendering sample fPSA nondetectable in a particular immunoassay can vary widely. In one aspect, such means can involve isolation or separation of sample fPSA from the remainder of the blood sample in which the immunoassay is performed. Such separation can result in physical separation of the fPSA fraction from the liquid test mixture or can result in isolation or sequestration of fPSA in situ in the test mixture. By way of example, fPSA can be separated and rendered nondetectable by passing the test sample through a column or other matrix of material which selectively removes fPSA such as by ion exchange adsorption, molecular sieve filtration, affinity binding, or the like, or by contacting the test sample with an immobilized or immobilizable form of fPSA-specific antibody, such as anti-fPSA fixed to a magnetic or latex particle.

In another aspect, fPSA is rendered nondetectable by immunoassay by treatment of the test sample with physical, chemical (including biochemical), or other means which convert or modify the relevant antigenic determinant(s) sufficiently to render fPSA substantially incapable of binding with antibody involved in the PSA immunoassay. The PSA immunoassay can then be performed directly in the resulting test mixture. By way of example, such treatment can involve differential denaturation of fPSA and cPSA such as by heating or cooling; addition of a chemical denaturant which denatures fPSA antigenic determinants (E-epitope), while being ineffective against cPSA determinants which are protected by complexation, such as proteases specific for peptides unique for the E-epitope region and the like; addition of a biochemical agent which binds or otherwise blocks the E-epitope region such as protein or lipid binders, substrate mimics (e.g., peptides which resemble a normal substrate recognized by an enzymatic site in the E-epitope region, but which bind without subsequent enzymatic cleavage or reaction); and the like. The above means for accomplishing the desired immunological inactivation of fPSA are not intended to be exhaustive and other effective methods will be evident to the ordinary worker in the field.

A particularly unique method for determining cPSA provided by the present invention involves an ingenious modification of a conventional two-site immunometric assay. In this new method, one of the capture and detection antibodies is selected to be capable of binding tPSA (that is, it binds to an epitope that is available on both fPSA and cPSA), but substantially incapable of binding to PSA when PSA is bound by a fPSA-specific antibody (i.e., an anti-E antibody). This unique antibody is referred to herein as MM1. Thus, by adding anti-E as a third antibody, fPSA which becomes bound by anti-E is rendered substantially incapable of binding to MM1, and thus substantially incapable of being detected in a two-site immunometric assay based on MM1.

In this particularly preferred method, the second antibody (the MM1 antibody) and the third antibody (the anti-E antibody) independently are each preferably a mono-specific antibody (e.g., a monoclonal antibody or a polyclonal antibody obtained by a conventional antiserum method which has been prepared such that the antibody fraction consists essentially only of antibodies that bind to the specific epitope of interest), and most preferably is a monoclonal antibody. Moreover, the anti-E antibody can, if desired, comprise more than one antibody, e.g., more than one monoclonal antibody, in order to obtain the desired inhibition of MM1. It will be further understood that the desired degree of inhibition of binding of the MM1 antibody to fPSA caused by the binding of the anti-E antibody (or antibodies) will normally be greater than about 90%, more usually greater than about 95%, and most preferably greater than about 99%.

Particularly preferred monoclonal MM1 antibodies can be prepared in a number of ways. Principally, the monoclonal antibody will be prepared by applying conventional somatic cell hybridization techniques using a screening method for selection of hybridoma cell lines which results in isolation of hybridomas which produce a monoclonal antibody having the defined binding properties of MM1. The strategy for such screening is to select antibodies that block the binding of other antibodies directed to epitopes accessible on fPSA but not cPSA, e.g., E-epitope, but themselves have substantially equivalent binding to fPSA and cPSA.

Somatic cell hybridization is now a well-known methodology and can be applied to the present invention in all of its variations as appropriate and desired. In general, one prepares a population of hybridomas by fusion of myeloma cells with lymphocyte cells taken from an animal that has been immunized against the analyte. Immunization of the host animal, as used herein, implies that the animal's immune system has been challenged to produce antibodies that will bind to one or more epitopes on the analyte of interest. It will be evident to the skilled worker in the art that such result can be obtained in any number of ways, including, without limitation, administration of the native analyte, synthetic peptide immunogen, tranfectant cells which express epitopes of the analyte on their surface, or the like, to the bloodstream of the host animal. Similarly, production and harvesting of monoclonal antibodies from cloned hybridoma cell lines are within the ordinary skill in the art, and in general any known method can be used in practicing the present invention.

As described above, the principal criteria for screening of hybridomas to produce a monoclonal antibody having MM1 characteristics are that it produce a monoclonal antibody which (i) binds substantially equivalently to fPSA and cPSA, but (ii) is substantially incapable of binding to PSA when PSA is bound by a fPSA-specific antibody (an anti-E antibody). Alternatively, but less preferably, the screening criteria can be that it produce a monoclonal antibody which (i) binds substantially equivalently to fPSA and cPSA, but (ii) upon becoming bound to PSA, renders PSA substantially incapable of binding to antibodies that are specific for fPSA, that is, antibodies that can bind fPSA, but not cPSA. The mechanism by which the MM1 monoclonal antibody of the present invention operates to provide the above result is not clearly understood; however, it is speculated that the binding of the monoclonal antibody to fPSA (i.e., anti-E antibody) blocks, masks, obscures, or alters the epitope(s) that are available on both fPSA and cPSA for binding by an antibody or antibodies directed to such epitope(s). Representative of the MM1 monoclonal antibody employed in the present invention are the MM1 antibody used in the Bayer Immuno 1™ PSA Assay (Bayer Corporation, Tarrytown, N.Y., USA); the monoclonal antibodies produced by hybridoma cell lines 346.7.4 and 346.7.26 deposited by the assignee of the present application (Bayer Corporation) with the American Type Culture Collection, 10801 University Boulevard, Manassas, Va. 20110-2209 Rockville, Md., USA, on Apr. 10, 1997, and assigned deposit numbers HB-12338 and HB-12337, respectively; and monoclonal antibodies that bind to substantially the same epitope as any of the aforesaid antibodies.

The reagents and other assay components necessary for practice of the above-described particularly preferred method for determining cPSA are conveniently provided in the form of a test kit, that is, a packaged collection or combination as appropriate for the needs of the user and any analytical instrumentation involved. Minimally, the test kit will comprise the particularly characterized capture and detection antibodies and one or more anti-E antibodies.

cPSA blood values in male patients have now been found to provide substantial clinical significance in comparison to the prior art tPSA values and fPSA/tPSA ratio values. Specifically, an initial study was conducted using serum samples from 216 patients including 53 patients with CaP, 75 patients with BPH, and 88 healthy male controls over the age of 50 years (infra, the data presented in FIG. 4A). In this initial study, the upper limit of normal of the cPSA assay was established to provide equivalent sensitivity for detection of CaP as compared with measurement of tPSA (85% v. 88%, respectively). For all patients tested, the specificity in the normal and BPH populations was also comparable for cPSA compared to the fPSA/tPSA ratio. These findings were confirmed in a subsequent study using serum samples from 300 biopsied patients from a urology referral population including 75 patients with CaP, and 225 patients found to be free of CaP by biopsy (infra, the data presented in FIG. 3B). The finding that the sensitivity and specificity of the tPSA assay used in conjunction with a fPSA/tPSA ratio is equivalent to that of the cPSA alone also held true when the patient population was stratified into the diagnostic gray zone. The precise range of the diagnostic gray zone has not been defined, but at all ranges compared in this study, the sensitivity and specificity of the cPSA assay was comparable to that obtained using both total and free PSA assays. These data demonstrate that a single test, cPSA, can detect prostate cancer as efficiently as total PSA, and, in addition, has the improved specificity that has been shown to be obtainable using two assays, fPSA and tPSA.

In the studies referred to above, the upper limit of normal (sometimes referred to as the cut-off value) selected for the cPSA assay data was 3.75 ng/mL (expressed as an equivalent PSA concentration). This upper limit of normal value was selected in order to achieve a sensitivity for CaP detection in the group of men with histologically confirmed cancer substantially similar to that provided using a 4.0 ng/mL cut-off with the tPSA assay (85% compared to 88% in the initial study and 81% compared to 83% in the subsequent study). It will of course be understood in the art that as larger sample populations are tested, the optimum upper limit of normal for cPSA values may shift to some degree, however, it would be anticipated that such optimum upper limit of normal will, in any event, fall approximately between 3–4 ng/mL (equivalent to approximately 9–12 ng/mL PSA-ACT). Selection of an upper limit of normal above 4 ng/mL would generally be understood to result in a clinically unacceptable level of sensitivity, while selection of an upper limit of normal below 3 ng/mL might be considered by some clinicians to afford increased sensitivity with an acceptable loss in specificity. However, it will be recognized that for any given level of sensitivity, the cPSA method of the present invention will provide, in a single assay result, a significantly improved level of specificity as compared with conventional tPSA methods, and an equivalent or improved level of specificity as compared with recently published methods based on the ratioing of two assay results, e.g., fPSA/tPSA. It is further contemplated that detection of prostate cancer in an asymptomatic male patient will be enhanced by serial measurement of cPSA over time as has been shown for serial tPSA measurements (29).

In addition to the above-discussed use in the detection of prostate cancer, the measurement of cPSA will be useful in the monitoring of the course of disease in patients who have been diagnosed with prostate cancer, particularly after having received first line therapy for prostate cancer. Longitudinal monitoring of such patients by measurement of tPSA has been proven to be useful in the early detection of recurrent prostate cancer. cPSA is understood to be the cancer-specific form of PSA and is the form that would be expected to increase in serum as cryptic cancer cells establish distant metastic sites and grow. Accordingly, changes in cPSA blood levels over time will correlate with changes in disease status, and particularly, increasing cPSA blood levels after therapy will indicate recurrence of disease.

Furthermore, since it is understood that cPSA is comprised primarily of PSA-ACT, the clinical significance and advantages of cPSA measurements extend to PSA-ACT measurements as well (as demonstrated in the study which produced the data presented in FIG. 6). In principle, immunoassay methods for the determination of PSA-ACT that would be most amenable for performance on instrumentation currently available would be two-site immunometric assays using anti-PSA antibody in combination with an anti-ACT antibody or an antibody that is specific for PSA-ACT complex. One method for attaining such latter antibody is by monoclonal selection of an antibody which is directed to a conformational epitope on the PSA-ACT complex, e.g., at or near the point on the surface of the complex where the ACT and PSA components meet. Presently, however, such methods are not well developed and/or suffer from analytical performance problems, and accordingly, until further improvements are forthcoming, measurement of PSA-ACT will require more cumbersome techniques. For example, as shown by Leinonen et al., PSA-ACT complexes may be separated by gel filtration (molecular sieve) chromatography and measured in assays which detect either tPSA or are specific for PSA-ACT (15).

The present invention will now be illustrated, but is not intended to be limited by, the following examples.

EXAMPLES

Materials. Anti-PSA antibodies used in these studies include MM1, a monoclonal antibody which recognizes an epitope expressed on free PSA and PSA complexed with proteinase inhibitors. The antibody was produced in mouse ascites fluids and purified by protein A affinity chromatography using standard procedures. MP2 is a polyclonal anti-PSA antibody which was produced in goats and purified by affinity chromatography on immobilized PSA. PSA 19, PSA 20, PSA 30 (CanAg Diagnostics AB, Gothenburg, Sweden) and ME2 (Biospacific, Emeryville, Calif., USA) are monoclonal antibodies which recognize the E-epitope of PSA. ACT 53 (CanAg Diagnostics) is an ACT-specific monoclonal antibody. Free prostate-specific antigen (Scripps Laboratories, San Diego, Calif., USA) was purified from human seminal fluid with 98% purity by sodium dodecyl sulfate-polyacrylamide gel electrophoresis and was stored in a buffer containing 10 mM Tris, 0.1% sodium azide, pH 8.0. PSA-ACT (Scripps Laboratories, San Diego, Calif., USA) showed>96% purity by sodium dodecyl sulfate-polyacrylamide gel electrophoresis, and was stored in a buffer containing 10 mM sodium acetate, 150 mM sodium chloride, and 0.1% sodium azide, pH 5.6.

The Bayer Immuno 1™ PSA Assay. The Bayer Immuno 1 total PSA (tPSA) assay is a sandwich assay which uses a monoclonal antibody for capture and a polyclonal antibody for detection of PSA. The monoclonal anti-PSA antibody (MM1) is conjugated to fluorescein (R1) and the affinity-affinity-purified polyclonal antibody (MP2) is conjugated to alkaline phosphatase (R2). The antibodies are diluted to 1.5 $\mu$g/ml for R1 and 6.15 $\mu$g/ml for R2 in a buffer containing 100 mM Tris-HCl, pH 7.4, and 5% heat-inactivated normal goat serum (Biocell Laboratories, Carson, Calif., USA). A 65 $\mu$L volume of each of the two antibodies are incubated with 20 $\mu$l of the test specimen in a reaction cuvette for 20 min at 37° C., and the resulting immunocomplex (R1-PSA-R2) is captured by the addition of magnetic particles coated with monoclonal anti-fluorescein antibodies (20 $\mu$L). After a wash step to remove excess reagents and sample components, 300 $\mu$l of 23 mM p-nitrophenyl phosphate is added. The rate of color formation is monitored by absorbance measurements at 405 or 450 nm and the rate of color formation is directly proportional to the concentration of PSA in the test specimen. Further details are provided in J. Clin. Lab. Anal. (1996), 10:155–159. Calibration of the Bayer Immuno 1 Analyzer is performed using the Bayer Immuno 1 SET point® PSA calibrators, prepared from free PSA at concentrations of 0, 2, 10, 25, 50 and 100 ng/mL. A cubic-through-zero fitting algorithm is used to generate a standard calibration curve.

The Bayer Immuno 1 Free PSA Assay. The protocol used for the Bayer Immuno 1 total PSA Assay described above was adapted for measurement of free PSA by the substitution of a monoclonal antibody specific for free PSA (PSA 19, CanAg) conjugated to fluorescein as the R1 capture antibody. The monoclonal anti-free PSA R1 was used with the same polyclonal anti-PSA alkaline phosphatase conjugate (R2) as that used in the total PSA Assay. The R1 conjugate was diluted to 2.5 $\mu$g/mL and the R2 was used at 6.15 $\mu$g/mL. Other conditions were similar to those used in the tPSA Assay except that the sample volume was 35 $\mu$l per test and the volume of magnetic particles added was 15 $\mu$L per test.

The Bayer Immuno 1 PSA-ACT Method. The Bayer Immuno 1 PSA-ACT assay format is the same as that of the Bayer Immuno 1 tPSA Assay except for the following changes: (1) a monoclonal antibody specific for ACT, ACT 53, is conjugated to alkaline phosphatase and used for detection at 2 $\mu$g/mL; (2) PSA-ACT is used as the calibrator and control antigen with the 50 mM MES buffer, 6% BSA, pH 5.8; and (3) a two-wash protocol is used such that antigen is first incubated with capture antibody, the resulting complexed is washed to remove unbound antigen and other serum components, and then the detection antibody is added.

RESULTS

Selection and Option of Specific Antibodies for Inhibition of Free PSA Immunoreactivity in the Total PSA Assay. The present invention is based on the observation that the total PSA Assay can be made specific for PSA-protease inhibitor complexes by the addition of an antibody to the E epitope of PSA. Four monoclonal antibodies, PSA 19, PSA 20, PSA 30, and ME2, specific for the E-epitope on the PSA molecule, were tested for their ability to decrease reactivity of free PSA in the total PSA Assay. The calibrators used in the total PSA Assay were prepared using 100% free PSA purified from seminal fluid. Anti-E antibodies, PSA 19, PSA 20 and PSA 30, were added to the 50 ng/ml PSA calibrator at concentrations of 0, 10, 25, 50, 100, and 200 $\mu$g/mL. After incubation at room temperature for 30 to 60 min these mixtures were run as unknown samples using the total PSA assay and the recovery of PSA was determined. As shown in FIG. 1A, each of the three monoclonal antibodies, PSA 19, PSA 20, and PSA 30 showed significant inhibition of free PSA reactivity in the total PSA Assay. This decreased immunoreactivity of free PSA was concentration dependent for each of the antibodies but only PSA 20 approached saturation. Of these three anti-E antibodies, PSA 20 gave the greatest decrease in signal for free PSA.

Figure 1B:
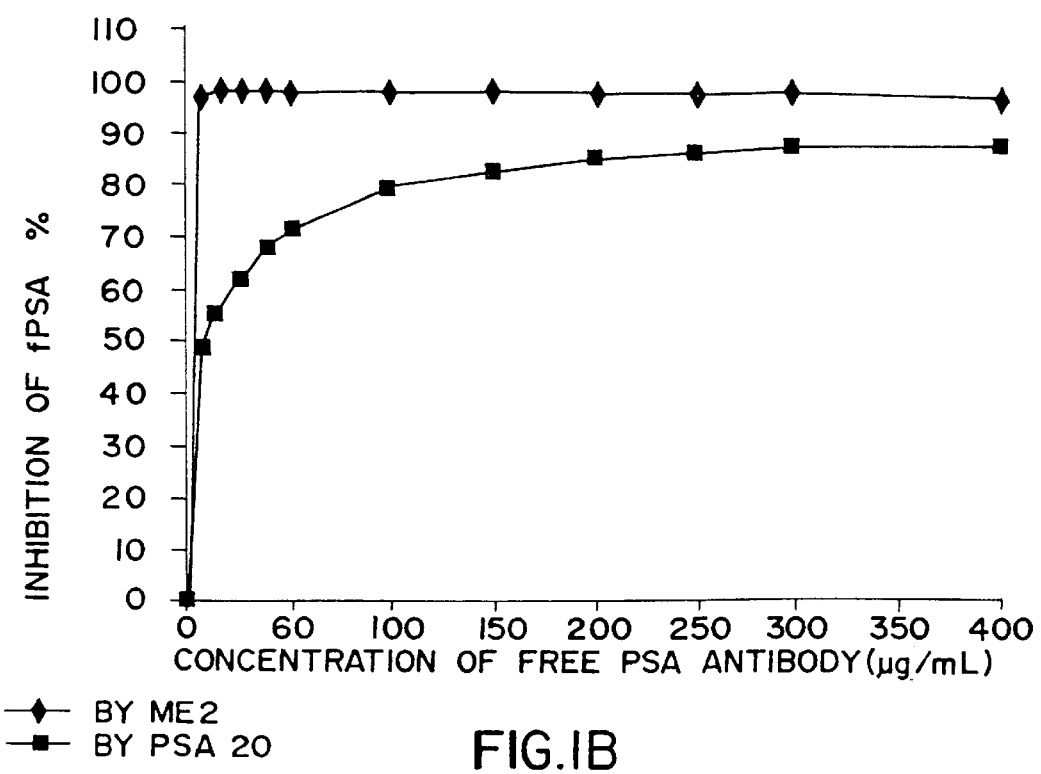
FIG. 1B shows a similar experiment in which two anti-E antibodies, PSA 20 and ME2, showed a concentration dependent inhibition of immunoreactivity of fPSA in the tPSA assay. Samples containing 10 ng/mL fPSA were preincubated with either the PSA 20 or ME2 MAb for 30–60 minutes and run in the Bayer Immuno 1 tPSA Assay.

In a separate experiment, PSA 20 and ME2 were compared for their ability to inhibit the binding of free PSA in the tPSA assay. Monoclonal antibodies were added to the 10 ng/ml calibrator at concentrations ranging from 0 to 400 $\mu$g/ml. As can be seen in FIG. 1B, the ME2 MAb inhibits the binding of free PSA in the total PSA quantitatively and reaches saturation at a concentration of less than 6.125 $\mu$g/mL. These data demonstrate that several E-epitope antibodies have the ability to inhibit the binding of the MM1 antibody to free PSA. However, the ME2 MAb inhibits free PSA binding in the total PSA assay at a much lower concentration and to a greater extent than other E-epitope antibodies. This inhibition could be due to a higher affinity of the ME2 antibody for the E-epitope. Alternatively, the E-epitope may represent a collection of epitopes with different fine epitope specificities.

Measurement of Complexed PSA on the Bayer Immuno 1 Analyzer. The addition of MAbs PSA 20 and ME2 to the total PSA Assay eliminates most of the immunoreactivity associated with free PSA. To demonstrate quantitative measurement of complexed PSA, mixtures with various proportions of free and ACT-complexed PSA were prepared at a total PSA concentration of approximately 11 ng/mL. The mixtures contained ratios of free:complexed PSA of 100:0, 80:20, 50:50, 20:80, and 0:100. These mixtures were measured using three immunoassay formats on the Bayer Immuno 1 Analyzer: the commercial assay for total PSA (tPSA), the Bayer Immuno 1 free PSA Assay (fPSA), and the Bayer Immuno 1 complexed PSA Assay (cPSA). The Bayer Immuno 1 complexed PSA assay was identical to the tPSA assay except that for results shown in FIG. 2A, PSA 20 MAb was added to each sample at a final concentration of 300 µg/ml and the MM1-fluorescein conjugate was reduced from 1.5 µg/ml to 0.5 µg/ml. For the experiment shown in FIG. 2B, the MAb ME2 was added to each sample at a final concentration of 25 µg/mL and the MM1-fluorescein conjugate was again used at 0.5 µg/mL. For the measurement of total PSA and free PSA, the Bayer Immuno 1 Analyzer was calibrated with the Bayer Immuno 1 SET point PSA calibrator set which is used commercially for the Bayer Immuno 1 total PSA Assay. To measure complexed PSA (cPSA), calibrators in the range of 0–100 ng/mL were prepared using PSA complexed with ACT in 50 mM MES, 6% BSA, pH 5.8.

Figure 2A:
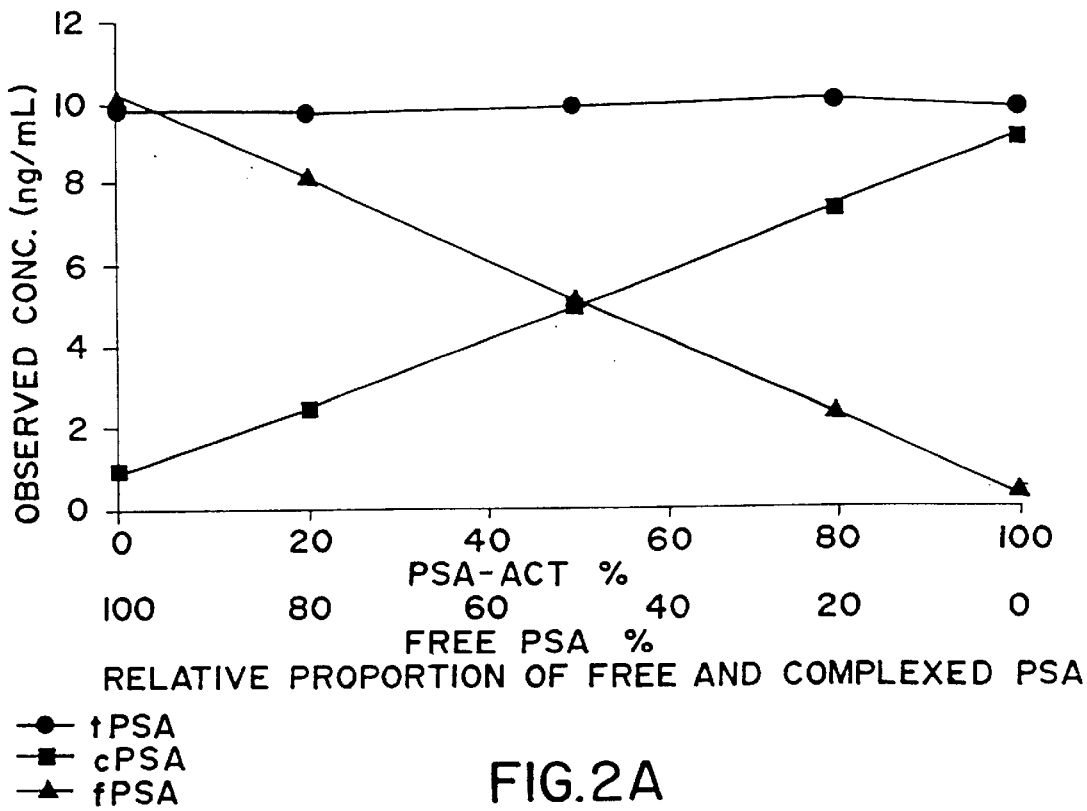
FIG. 2A is a graph showing that the addition of the anti-E antibody PSA 20 to the tPSA assay provides an immunoassay format for the measurement of cPSA. Samples containing approximately 11 ng/mL total PSA with varying proportions of free and complexed PSA were measured in the presence of 300 µg/ml MAb PSA 20 using the Bayer Immuno 1 analyzer.
Figure 2B:
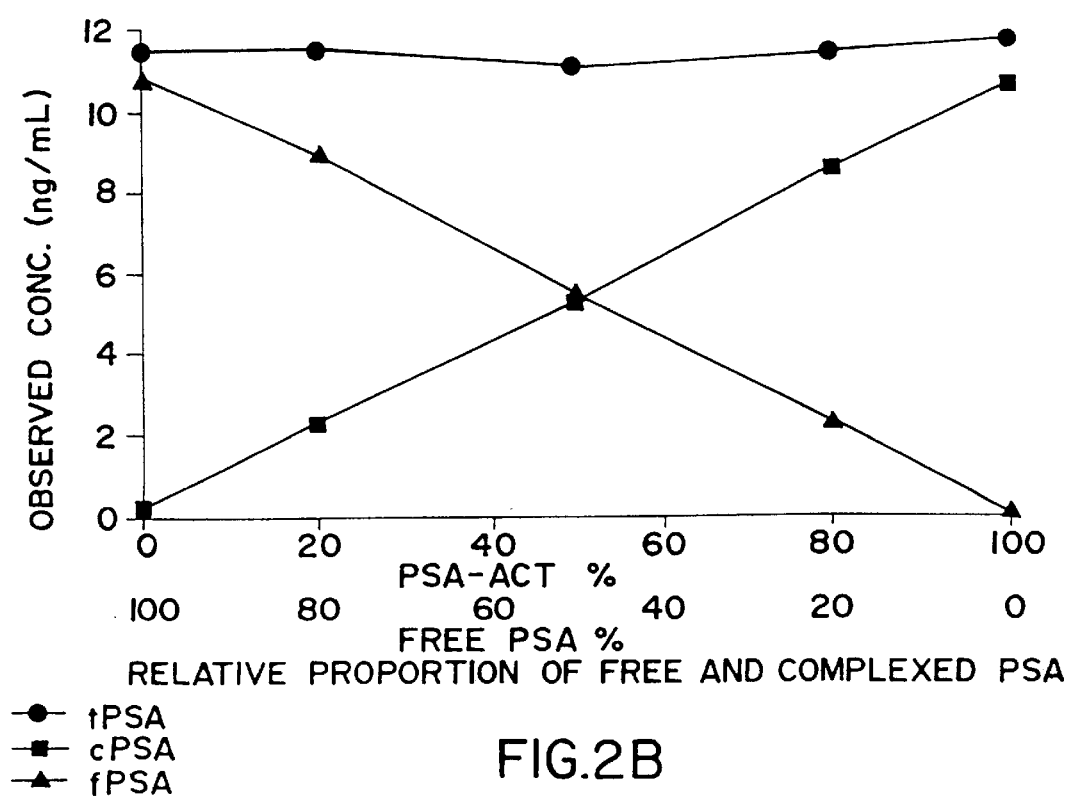
FIG. 2B is a similar graph showing that ME2 MAb can also be used to provide an immunoassay format for the quantitative measurement of cPSA. Samples containing approximately 11 ng/ml total PSA with varying proportions of free and complexed PSA were measured in the presence of 25 µg/mL MAb ME2 using the Bayer Immuno 1 analyzer.

The addition of MAb PSA 20 to the total PSA Assay provides a method with almost quantitative reactivity with complexed PSA (FIG. 2A). The response for the various mixtures in the cPSA assay was linear, and the measured concentration of total PSA and complexed PSA gave consistent recoveries of approximately 10 ng/mL for all samples tested, as expected. Similarly, MAb ME2 provides a method with quantitative reactivity with complexed PSA over the complete range of proportions of free and complexed PSA (FIG. 2B). In addition, the complexed PSA assay with MAb ME2 uses a significantly lower concentration of the ME2 MAb (25 µg/mL) compared with that required for the PSA 20 MAb (300 µg/mL). These data demonstrate that three antibodies which react with different epitopes on the PSA molecule (MM1, MP2, and either PSA 20 or ME2), can be used in combination to produce a method which accurately measures complexed PSA.

Automation of the cPSA Assay. Pretreatment of patient samples with MAb to the E-epitope is not practical for application in the clinical laboratory environment. Accurate dispensing of MAb into the sample is difficult and time consuming, and leads to an unacceptably high probability of inaccuracy in the result. Methods for fill automation of the cPSA Assay were therefore developed.

Automated MAb PSA 20 Methods. In assay format 1, MAb PSA 20 was added to the R2, MM1-fluorescein, reagent at a concentration of 500 µg/mL, and the assay was run as for the tPSA method using PSA-ACT for calibration. This assay takes 38 minutes for completion. In assay format 2, the sample is pretreated with MAb PSA 20 onboard. In this format, PSA 20 antibody was added to the reaction cuvette together with the patient sample and incubated for 50 minutes. MM1-fluorescein at a concentration of 0.5 µg/mL, MP2-ALP at a concentration of 6.15 µg/mL, and magnetic particles coated with anti-fluorescein antibodies were then added and incubated for an additional 28 minutes. After washing away excess reagents and unreacted serum, substrate was added and color formation was monitored in the same manner as for the tPSA Assay. Samples containing free PSA over a concentration range from 2 ng/ml–25 ng/ml were used. Results in FIG. 3 show that the signal with free PSA can be effectively reduced to very low levels using either of these approaches. These results suggest that this method can be fully automated on the Bayer Immuno 1 Analyzer.

Automated MAb ME2 Method. ME2 MAb inhibits the binding of the MM1 MAb to fPSA in the tPSA assay at a significantly lower concentration and to a greater degree than PSA 20 MAb. Additionally, assay format 2 takes a longer time and needs two reagent cassettes. Therefore, ME2 MAb was selected to be used as a third antibody for automation of the cPSA assay by addition into the tPSA assay in two ways—ME2 at a concentration of 50 and 100 ng/mL was added into either the reagent 1 (R1) or the reagent 2 (R2). Results showed that fPSA reactivity was inhibited 97% and 98% when ME2 was added into R1 and R2, respectively. Based on these data, it was determined that the cPSA assay would be formulated using ME2 MAb in the R2 reagent at a final concentration of 100 µg/mL.

Measurement of Complexed PSA in Serum.

Pilot Study.—Serum samples from 53 patients with prostate cancer, 75 patients with BPH, and 88 samples from healthy age-matched control subjects were analyzed using the three assays: tPSA, fPSA, and cPSA. Samples tested in the cPSA assay were pretreated with 25 µg/ml ME2 antibody, and samples tested in the fPSA and tPSA assays were untreated. The assays were calibrated using either free PSA or PSA-ACT complexes as described above. The results of this testing are shown in FIG. 4A. The upper limit of normal value of 3.75 ng/mL (expressed as an equivalent PSA concentration) was selected in order to achieve a sensitivity for CaP detection in the group of men with histologically confirmed cancer substantially similar to that provided using a 4.0 ng/mL cut-off with the tPSA assay (85% compared to 88%). With this upper limit of normal, the specificity in the normal and BPH populations tested in this study was also comparable for cPSA compared to a two-step test in which a positive tPSA result was followed by running a fPSA assay and calculating the fPSA/tPSA ratio. The finding that the sensitivity and specificity of the tPSA assay used in conjunction with a fPSA/tPSA ratio is equivalent to that of the cPSA alone, also held true when the patient population was stratified into the diagnostic gray zone. The precise range of the diagnostic gray zone has not been defined, but at all ranges compared in this study, the sensitivity and specificity of the cPSA assay was comparable to that obtained using both total and free PSA assays. These data demonstrate that a single test, cPSA, can detect prostate cancer as efficiently as total PSA, and, in addition, has the improved specificity that has been shown to be obtainable using two assays, fPSA and tPSA.

Figure 4C:
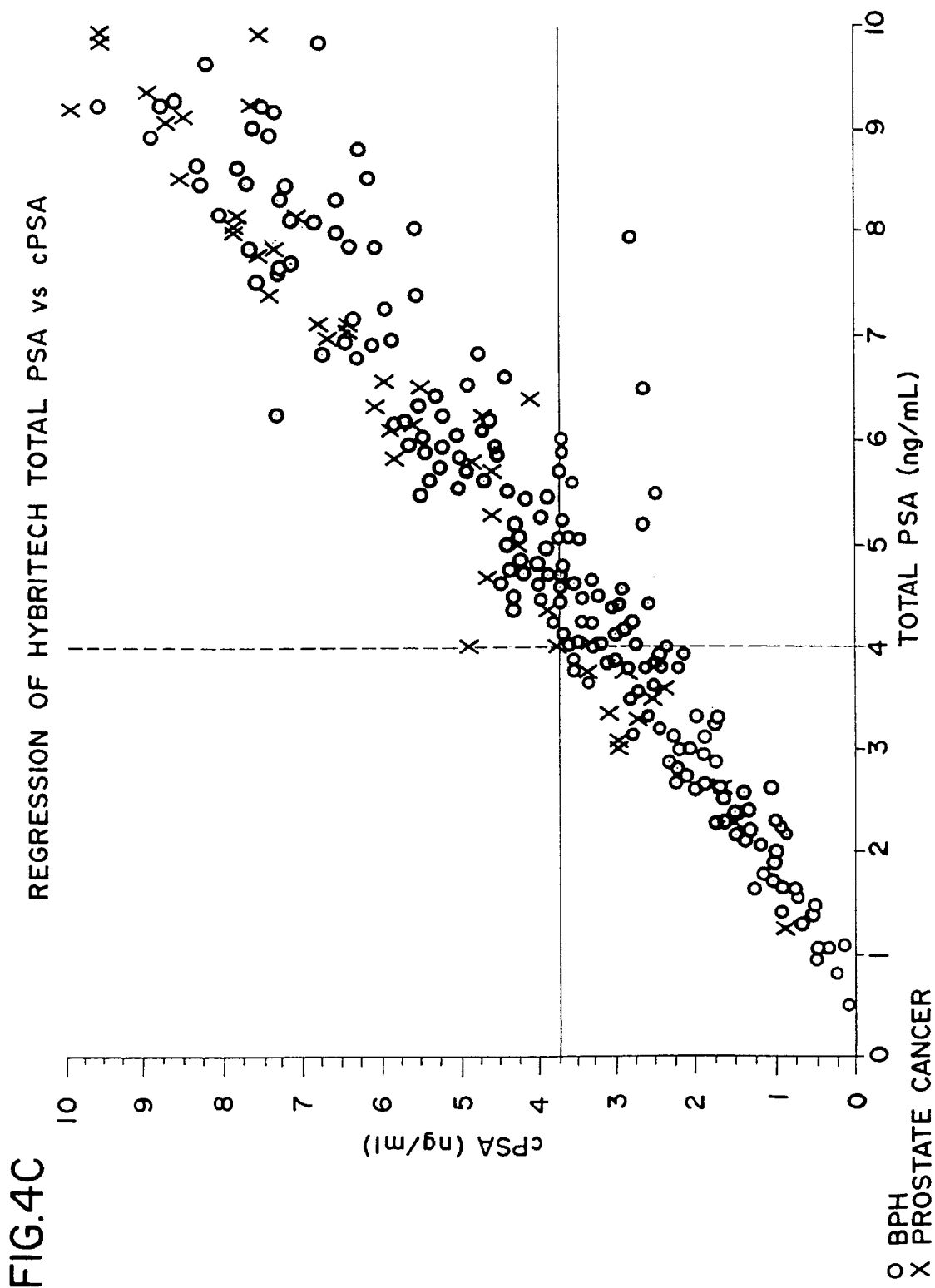
FIG. 4C is a graph of a regression analysis of results obtained using a commercial assay for total PSA compared to results obtained using the preferred cPSA assay for patient samples collected from men with prostate cancer and benign prostate disease.
Figure 5A:
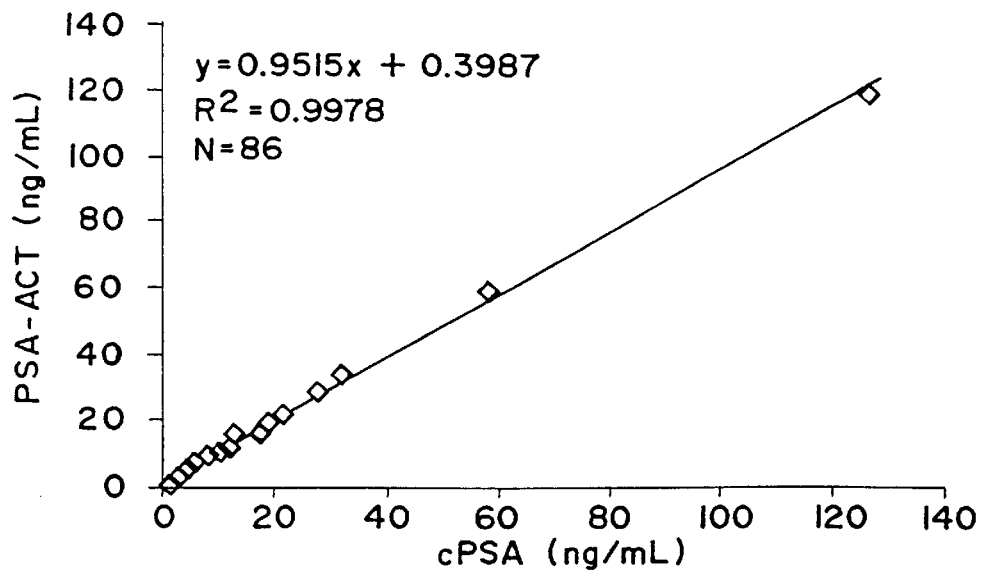
FIGS. 5A–5F are graphs showing the correlation between cPSA assay values and PSA-ACT assay values obtained from the testing of sera of men with cancer, BPH and in the normal population.
Figure 5B:
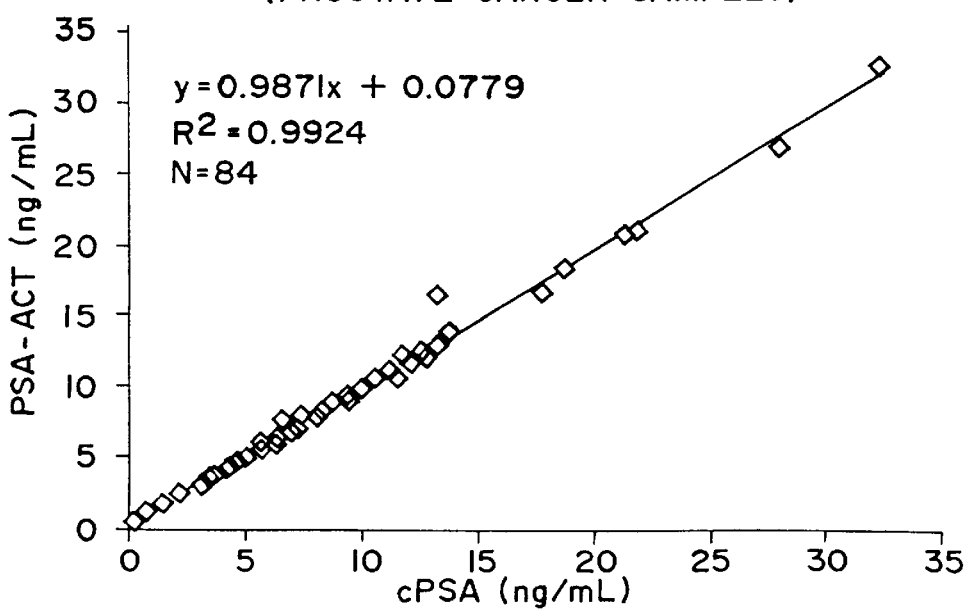
Figure 5C:
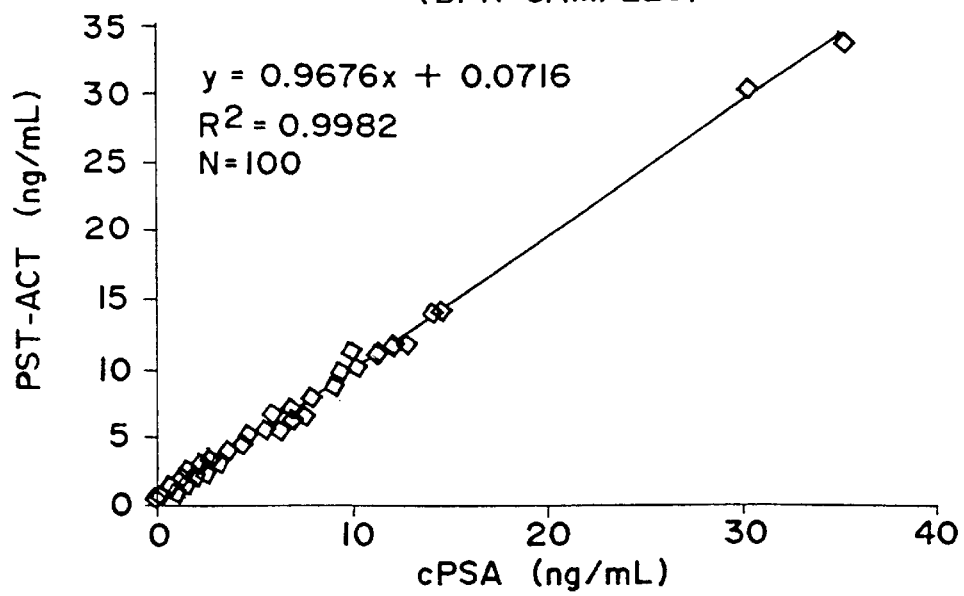
Figure 5D:
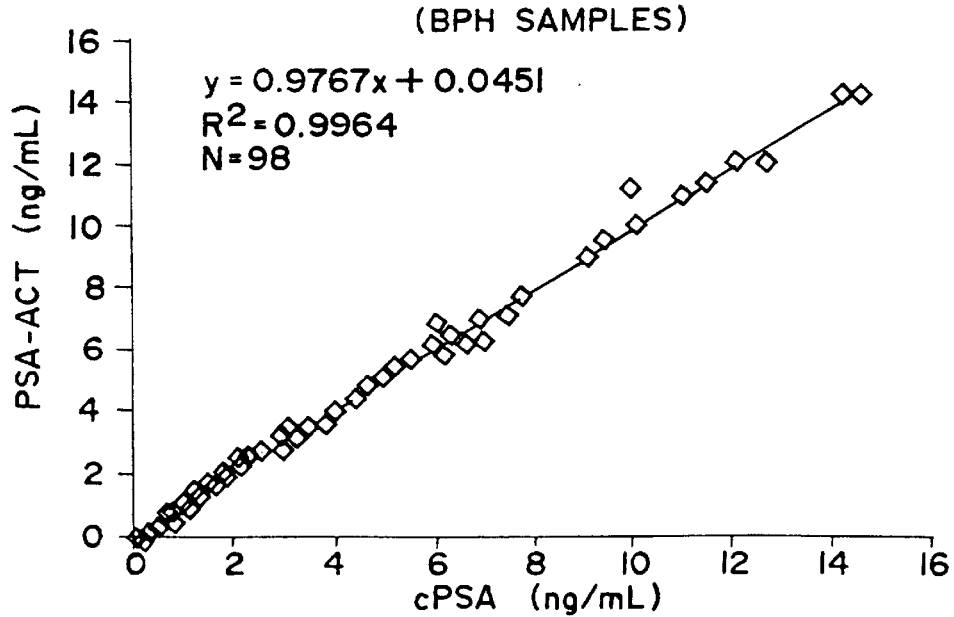
Figure 5E:
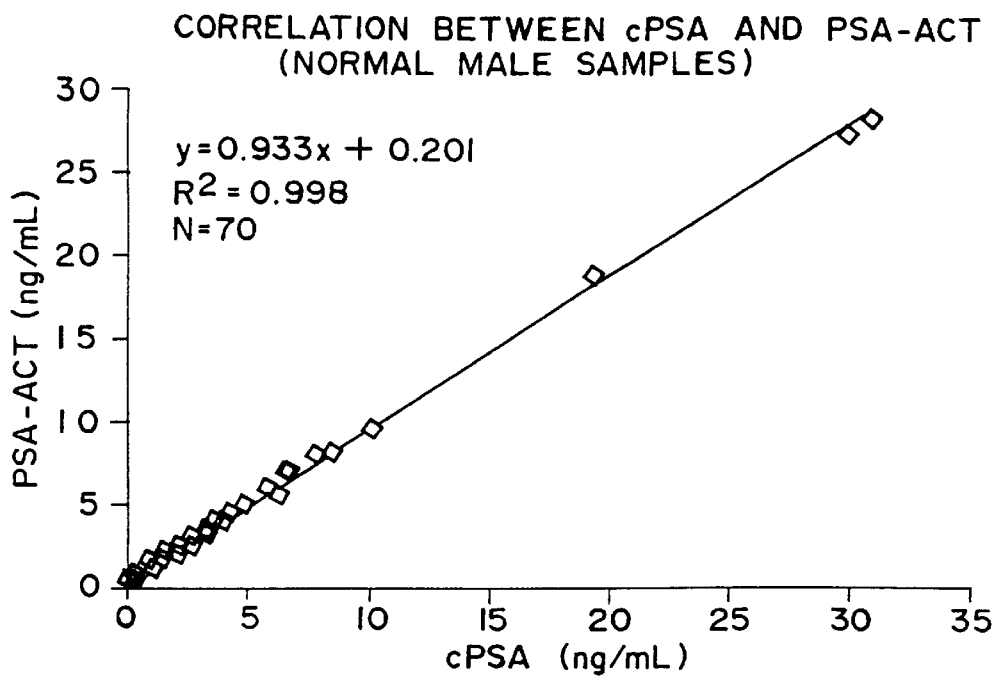
Figure 5F:
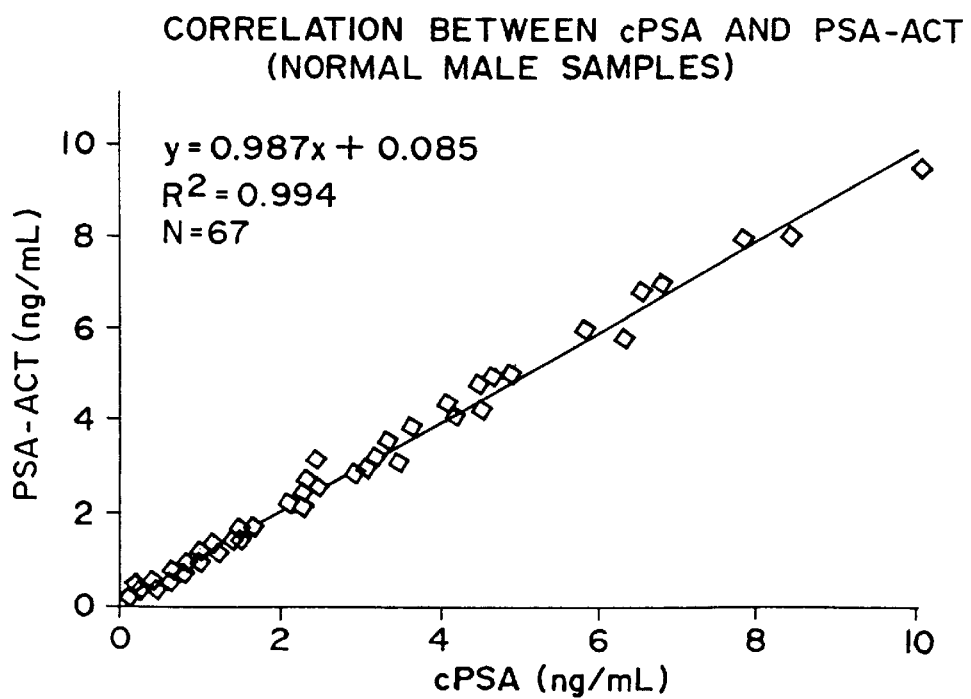

Clinical Study.—Serum samples from 300 biopsied patients (75 with confirmed prostate cancer) were analyzed at the Seattle VA Hospital, Seattle, Wash., USA using the three assays: tPSA (using the Hybritech Tandem® PSA Assay, San Diego, Calif., USA), fPSA (using the Hybritech Tandem® free PSA Assay), and cPSA (using the automated MAb ME2 method described above). The assays were calibrated using either free PSA or PSA-ACT complexes as described above. The results of this testing are shown in table form in FIG. 4B and as a regression analysis in FIG. 4C. The upper limit of normal value of 3.75 ng/mL (expressed as an equivalent PSA concentration) was again selected in order to achieve a sensitivity for CaP detection in the group of men with histologically confirmed cancer substantially similar to that provided using a 4.0 ng/mL cut-off with the tPSA assay (81% compared to 83%). With this upper limit of normal, the specificity in the normal and BPH populations tested in this study was also comparable for cPSA compared to the two-step test (supra, tPSA+fPSA/ tPSA). In FIG. 4C, the small circle data points appearing in the lower right quadrant of the graph represent those non cancer patients (34 out of 117, or 29%) who would have avoided the risk, discomfort and expense of biopsy had their cPSA, rather than their tPSA, value been used as the basis of this medical decision. Also, as in the pilot study, the finding that the sensitivity and specificity of the tPSA assay used in conjunction with a fPSA/tPSA ratio is equivalent to that of the cPSA alone, held true when the patient population was stratified into the diagnostic gray zone (supra).

The data from the independent pilot and clinical studies demonstrate that a single test, cPSA, can detect prostate cancer as efficiently as total PSA, and, in addition, has the improved specificity that has been shown to be obtainable using two assays, fPSA and tPSA.

Correlation Between cPSA and PSA-ACT. To determine what species of complexed PSA are measured in the cPSA assay, an assay was developed to measure PSA completed with ACT. This species of completed PSA has been reported to represent the predominant form of complexed PSA in serum. Previous attempts to measure PSA-ACT using manual methods have met with technical difficulties as discussed above. Accordingly, an automated immunoassay was developed for measuring PSA-ACT complexes on the Bayer Immuno 1™ system. The same population of patients described above in the pilot study were tested using the automated assay for PSA-ACT. Results are shown in FIGS. 6A–6F where results obtained using the automated PSA-ACT assay are regressed against results obtained using the automated cPSA assay. For each patient population, i.e., normals, prostate cancer, and benign prostate disease (BPH), regression analysis was done for all patient samples, and over the range containing the majority of patient test results. This was done to eliminate bias in the regression analysis due to a small number of high values. In any event, the slopes of the regressions ranged from 0.93–0.98. These data suggest that approximately 93–98% of the substances measured by the cPSA assay is PSA-ACT. The biochemical nature of the remaining 2–7% of cPSA is not known at this time.

Specificity of PSA Assays at Selected Sensitivities. The upper limit of normal used for the cPSA assay was determined to give similar sensitivity as the tPSA assay. Using this cut-off value, it was demonstrated that the cPSA assay provides improved specificity over methods currently used in medical practice, i.e., tPSA. The specificity of the cPSA assay was also measured using different values for the upper limit of normal. All results derived from the clinical study described above were used in a Receiver Operator Characteristic (ROC) analysis. Specificity was then determined from the ROC analysis at varying levels of sensitivity ranging from 80–100%. Sensitivities of less than 80% have little medical value since diagnostic methods in current practice provide at least this level of sensitivity. Results shown in FIG. 7 demonstrate that at all levels of sensitivity, the cPSA assay provides additional sensitivity over tPSA and approximately equivalent or slightly better specificity than the use of two assays, tPSA and fPSA. In addition, the improvement in specificity holds true even when the patient samples are stratified in the diagnostic gray zone. These results further demonstrate that the upper limit of normal for the cPSA assay can be chosen over a broad range, depending on the desired level of sensitivity and specificity, but at all values for the upper limit of normal ranging between about 3–4 ng/mL, cPSA gives improved specificity over tPSA, and approximately equivalent specificity as the fPSA/tPSA ratio.

The present invention has been particularly described and exemplified above. Clearly, many other variations and modifications of the invention can be made without departing from the spirit and scope hereof.

BIBLIOGRAPHY

1. Wang M. C., Valenzuela L. A., Murphy G. P., Chu T. M. Purification of a human prostate specific antigen. Invest Urol 1979; 17: 159–63.
2. Watt W. K., Lee P. J., Timkulu T. M., Chan W. P., Loor R. Human prostate-specific antigen: structure and functional similarity with serine proteases. Proc Natl Acad Sci USA 1986; 83:3166–70.
3. Akiyama K., Nakamura T., Iwanaga S., Hara M. The chymotrypsin-like activity of human prostate-specific antigen, r-seminoprotein. FEBS Letters 1987; 225:168–72.
4. Christensson A., Laurel C. B., Lilja H. Enzymatic activity of prostatic-specific antigen and its reactions with extracellular serine proteinase inhibitors. Eur J Biochem 1990; 194:755–763.
5. Lilja H. A kallikrein-like serine protease in prostatic fluid cleaves the predominant seminal vesicle protein. J Clin Invest 1985; 76:1899–903.
6. Lilja H., Abrahamsson P. A. Three predominnant proteins secreted by the human prostate gland. Prostate 1980; 12:29–38.
7. Papsidero L. D., Wang M. C., Valenzuela I. A., Murphy G. P., Chu T. M. A prostate antigen in sera of prostate cancer patients. Cancer Res 1980; 40:2428–2432.
8. Lange P. H. Prostate specific antigen in diagnosis and management of prostate cancer. Supplement to Urology 1990; XXXVI:25–29.
9. Oesterling J. E. Prostate specific antigen: a critical assessment of the most useful tumor marker for adenocarcinoma of the prostate. J Urol 1991; 145:907–923.
10. Armbruster DA. Prostate-specific antigen: biochemistry, analytical methods and clinical application. Clin Chem 1993; 39:181–195.
11. American Cancer Society: Cancer facts & figures—1995. American Cancer Society, Inc., Atlanta, Ga. Page 11.
12. Catalona W. J., Richie J. P., Ahmann F. R., Hudson M. A., Scardino P. T., Flanigan R. C., deKernion J. B., Ratliff T. L., Kavoussi L. R., Dalkin B. L., Waters, W. B., MacFarlane M. T. and Southwick P. C. Comparison of digital rectal examination and serum prostate specific antigen in the early detection of prostate cancer: results of a multicenter clinical trial of 6,630 men. J Urol 1994; 151:1283–1290.
13. Stenman U. H., Leinonen J., Alfthan H., Rannikko S., Tuhlkanen K., Alfthan O. A complex between prostate-specific antigen and $\alpha 121$-antichymotrypsin is the major form of prostate-specific antigen in serum of patients with prostatic cancer: assay of the complex improves clinical sensitivity for cancer. Cancer Res 1991; 51:222–226.
14. Zhou A. M., Tewari P. C., Bluestein B. L., Caldwell, G. W., Larsen F. L. Multiple forms of prostate-specific antigen in serum: differences in immunorecognition by monoclonal and polyclonal assays. Clin Chem 1993; 39:2483–91.
15. Leinonen J., Lovgren T., Vornanen T., Stenman U. H. Double-label time-resolved immunofluorometric of prostate-specific antigen and its complex with $\alpha_1$-antichymotrypsin. Clin Chem 1993: 39:2098–2103.

16. Christensson A., Bjork T., Nilsson O., Nilsson O., Dahlen U., Matikainen M. T., Cockett A. T., Abrahamssion P. A. Serum prostate specific antigen complexed with $\alpha_1$-antichymotrypsin as an indicator of prostate cancer. J Urol 1993; 150:100–105.

17. Lilja H., Significance of different molecular forms of serum PSA. The free, noncomplexed forms of PSA versus that complexed to $\alpha_1$-antichymotrypsin. Urol Clin North Am 1993; 20(4):681–686.

18. Lilja H., Christensson A. Dahlen U., Matikainen M-T., Nilsson O., Pettersson K. and Lovgren T.: Prostate-specific antigen in human serum occurs predominantly in complex with alpha-antichymotrypsin. Clin Chem 1991; 37:1618–1625.

19. Bjork T., Hulkko S., Bjartell A., Santagnese A. D., Abrahamsson P-A., Lilja H. Alpha$_1$-antichymotrypsin production in PSA-producing cells is common in prostate cancer but rare in benign prostatic hyperplasia. Urology 1994; 43:427–434.

20. Pettersson K., Piironen T., Seppala M., Liukkonen L., Christensson A., Matikainen M-T., Suonpaa M., Lovgren T., Lilja H. Free and complexed prostate-specific antigen (PSA): in vitro stability, epitope map, and development of immunofluorometric assays for specific and sensitive detection of free PSA and PSA-$\alpha_1$-antichymotrypsin complex. Clin Chem 1995; 41:1480–1488.

21. Wu J. T., Wilson L., Zhang P., Meikle A. W., Stephenson R. Correlation of serum concentrations of PSA-ACT complex with total PSA in random and serial specimens from patients with BPH and prostate cancer. J Clin Lab Anal 1995 9:15–24.

22. Mitrunen K., Pettersson K., Piironen T., Bjork T., Lilja H., Lovgren T. (1995) Dual label one-step immunoassay for simultaneous measurement of free and total prostate specific antigen concentrations and ratios in serum. Clin Chem 1995 41(8):1115–1120.

23. Catalona W. J., Smith D. S., Wolfert R. L., Wang T. J., Rittenhouse H. G., Ratliff T. L., Nadler R. B. Evaluation of percentage of free serum prostate-specific antigen to improve specificity of prostate cancer screening. JAMA 1995 274(15): 1214–1220.

24. Prestigiacomo A. F., Stamey T. A. Clinical usefulness of free and complexed PSA. Scan J Clin Lab Invest 1995 55Supple221:32–34.

25. Wang T. J., Hill T. M., Sokoloff R. L., Frankenne F. Rittenhouse H. G., Wolfert R. L. Dual monoclonal antibody immunoassay for free prostate-specific antigen. Prostate 1996 28:10–16.

26. Jung K., Stephan C., Lein M., Henkne W., Schnorr D., Brux B., Schurenkamper P., Loening S. A. Analytical performance and clinical validity of two free prostate-specific antigen assays compared. Clin Chem 1996 42(7):1026–1033.

27. Wang T. J., Hill T., Sokoloff R., Frankenne F., Wolfert R., and Rittenhouse H. Monoclonal antibody sandwich immunoassay to quantitate free PSA in benign hyperplasia and prostate cancer. Poster presentation at 1994 ISOBM meeting.

28. Chan D., Kelley C. A., Partin A. W., Linton J., Wang T. J., Sokoloff R. L., Rittenhouse H. G., and Wolfert R. L. Clin Chem (1996) 42(6):S255.

29. Wang T. J., Linton J., Payne J., Rittenhouse H. G., Wolfert R. L., Chan D. W., Kelley C. A. and Partin A. W. Clinical utility of a complexed PSA immunoassay with a specific monoclonal antibody to PSA-ACT. J Urology (1997) 157(4) Suppl:147.

30. Wang T. J., Linton H. J., Payne J., Liu R-S., Kuus-Reichel K., Rittenhouse H. G., Kelley C., Cox J., Chan D. W., and Wolfert R. L. Development of monoclonal antibodies specific for the PSA-ACT complex and their incorporation into an immunoassay. Clin Chem (1997) 43(6):S225.

31. Zhang P. and Wu, J. T. Development of an immunoassay for the PSA-ACT complex in serum without interference of non-specific adsorption. Clin Chem (1997) 43(6):S236.

32. Bjork T., Bjartell A., Abrahamsson P-A., Hulkko S., Di Sant'agnese A., Lilja H. Alpha$_1$-antichymotrypsin production in PSA-producing cells is common in prostate cancer but rate in benign prostatic hyperplasia. Urol 1994 43(4):427–434.

33. Carter H. B., Pearson J. D., Metter J., Brant L. J., Chan D. W., Andres R., Fozard J. L. and Walsh P. C. Longitudinal evaluation of prostate-specific antigen levels in men with and without prostate disease. JAMA 1992 267(16):2215.

What is claimed is:

1. A method for determining complexed prostate specific antigen (cPSA) in a blood sample, comprising the steps of:
   (a) contacting said blood sample with three anti-PSA antibodies to form a liquid test mixture:
      (i) a first anti-PSA antibody which binds to total PSA (tPSA),
      (ii) a second anti-PSA antibody which binds to tPSA, but which is substantially incapable of binding to PSA when PSA is bound by an antibody that binds to free PSA (fPSA) but not to cPSA, wherein one of said first and second antibodies is labeled ("labeled antibody") and the other is immobilized or capable of being immobilized for purposes of separation from the liquid test mixture ("capture antibody"), and
      (iii) a third anti-PSA antibody, which third antibody binds to fPSA but not to cPSA, whereby binding of said third antibody to fPSA renders fPSA substantially incapable of being detected in the method,
   (b) separating said capture antibody from the liquid test mixture, and
   (c) measuring the label in the separated capture antibody phase or the remainder of the liquid test mixture.

2. The method of claim 1 wherein said second anti-PSA antibody is a monoclonal antibody.

3. The method of claim 2 wherein said third anti-PSA antibody is a monoclonal antibody.

4. The method of claim 3 wherein said monoclonal third anti-PSA antibody binds to substantially the same epitope as the monoclonal antibody produced by the cell line ATCC HB-12337 or HB-12338.

5. The method of any one of claims 1–4 wherein said first anti-PSA antibody is a polyclonal antibody.

6. The method of any one of claims 1–4 wherein said first anti-PSA antibody is a monoclonal antibody.

7. The method of claim 1 wherein said third anti-PSA antibody is contacted with said blood sample a predetermined period of time before said blood sample is contacted with either of said first and second anti-PSA antibodies.

8. The method of claim 1 wherein said third anti-PSA antibody is contacted with said blood sample substantially simultaneously with one or both of said first and second anti-PSA antibodies.

9. The method of claim 1 wherein the labeled antibody is labeled with an enzyme.

10. The method of claim 1 wherein the capture antibody is immobilized on a solid carrier.

11. The method of claim 1 wherein the capture antibody is modified with a ligand and is capable of being immobilized by contact with a binding partner for the ligand fixed to a solid carrier.

12. A test kit for use in determining complexed prostate specific antigen (cPSA) in a blood sample, comprising:
   (1) a first anti-PSA antibody which binds to total PSA (tPSA),
   (2) a second anti-PSA antibody which binds to tPSA, but which is substantially incapable of binding to PSA when PSA is bound by an antibody that binds to free PSA (fPSA) but not to cPSA, wherein one of said first and second antibodies is labeled and the other is immobilized or capable of being immobilized for purposes of separation from an aqueous liquid test mixture, and
   (3) a third anti-PSA antibody, which third antibody binds to fPSA but not to cPSA.

13. The test kit of claim 12 wherein said second anti-PSA antibody is a monoclonal antibody.

14. The test kit of claim 12 wherein said third anti-PSA antibody is a monoclonal antibody.

15. The test kit of claim 14 wherein said monoclonal third anti-PSA antibody binds to substantially the same epitope as the monoclonal antibody produced by the cell line ATCC HB-12337 or HB-12338.

16. The test kit of any one of claims 12–15 wherein said first anti-PSA antibody is a polyclonal antibody.

17. The test kit of any one of claim 12–15 wherein said first anti-PSA antibody is a monoclonal.

18. The test kit of claim 12 wherein the labeled antibody is labeled with an enzyme.

19. The test kit of claim 12 wherein the antibody that is immobilized or capable of being immobilized is immobilized on a solid carrier.

20. The test kit of claim 12 wherein the antibody that is immobilized or capable of being immobilized is modified with a ligand and is capable of being immobilized by contact with a binding partner for the ligand fixed to a solid carrier.

* * * * *